United States Patent [19]

Pessa et al.

[11] Patent Number: 5,625,058
[45] Date of Patent: Apr. 29, 1997

[54] PROCESS FOR THE PREPARATION OF CEPHALOSPORINS

[75] Inventors: Artemio Pessa, Peschiera Borromeo; Antonio Lerpini, San Martino Siccomario, both of Italy

[73] Assignee: Farmabios S.r.l., Italy

[21] Appl. No.: 273,841

[22] Filed: Jul. 12, 1994

[30] Foreign Application Priority Data

Jul. 16, 1993 [IT] Italy .................. MI93A1580

[51] Int. Cl.$^6$ .................................................. C07D 501/06
[52] U.S. Cl. ............................................ 540/226; 540/227
[58] Field of Search ........................... 540/222, 221, 540/227, 226

[56] References Cited

U.S. PATENT DOCUMENTS

| | | | |
|---|---|---|---|
| 4,048,311 | 9/1977 | Berges | 424/246 |
| 4,093,723 | 6/1978 | Berges | 424/246 |
| 4,139,701 | 2/1979 | Berges | 544/26 |
| 4,159,373 | 6/1979 | Berges | 544/26 |
| 4,576,937 | 3/1986 | Polansky | 514/204 |

FOREIGN PATENT DOCUMENTS

| | | |
|---|---|---|
| 0383811 | 9/1983 | Austria . |
| 0156771 | 10/1989 | European Pat. Off. . |
| 92/17600 | 10/1992 | WIPO . |

*Primary Examiner*—John M. Ford
*Attorney, Agent, or Firm*—Hedman, Gibson & Costigan, P.C.

[57] ABSTRACT

The present invention relates to a process for the preparation of 7-(α-hydroxyacylamino)-3-(1-sulphoalkyl-tetrazol-5-yl-thiomethyl)-3-cephem-4-carboxylic acids and relevant salts, via acylation of a 7-amino-3-(1-sulphoalkyl-tetrazol-5-yl-thiomethyl)-3-cephem-4-carboxylic acid with the corresponding chloride of α-formyl oxycarboxylic acid in a diluent, at pH 6.5–7.0; deformylation by treatment with an acid at pH between 0.5 and 1.5; extraction/s with an organic solvent of the acid aqueous phase from deformylation, followed by salting out and extraction with a solvent selected among tetrahydrofuran, methylethylketone, and acetonitrile; solvent evaporation and salification in a non-aqueous medium.

55 Claims, No Drawings

PROCESS FOR THE PREPARATION OF CEPHALOSPORINS

FIELD OF THE INVENTION

The present invention relates to a process for the preparation of cephalosporins, in particular of 7-(α-hydroxyacylamino)-3-(1-sulphoalkyl-tetrazol-5-yl-thiomethyl)-3-cephem-4-carboxylic acids and relevant salts.

PRIOR ART 7-(α-hydroxyacylamino)-3-(1-sulphoalkyl-tetrazol-5-yl-thiomethyl)-3-cephem-4-carboxylic acids belong to a group of cephalosporins possessing antibacterial activity, as is disclosed in U.S. Pat. Nos. 4,048,311, 4,093,723, and 4,159,373.

Among said cephalosporins, the 7-D-mandelamido-3-(1-sulphomethyltetrazol-5-yl-thiomethyl)-3-cephem-4-carboxylic acid, also known as Cefonicid, proved to be particularly interesting because of its potent antibacterial activity and satisfactory pharmacokinetic properties.

Cefonicid is available commercially as disodium salt under the trademark Monocid®; its monosodium salt is also known and is disclosed in U.S. Pat. No. 4,576,937.

The aforementioned U.S. patents report the synthesis of various 7-α-hydroxyacylamino-3-tetrazolylthiomethyl cephalosporins having the heterocyclic ring substituted with sulphonic or sulphamoyl groups. A first method envisages the acylation of 7-aminocephalosporanic acid (7-ACA) with an appropriately protected acylating agent, followed by condensation with the desired tetrazole thiol with subsequent removal of the protective groups.

An alternative method consists in condensing 7-ACA, protected e.g. as 7-formamido derivative, with tetrazole thiol, removing the formyl group by treatment with acids, and acylating the resulting 7-amino-3-tetrazolylthiomethyl cephalosporanic nucleus with a protected acylating agent.

In particular, U.S. Pat. No. 4,159,373 exemplifies the preparation of various 7-(α-hydroxyacylamino)-3-(1-sulphoalkyl-tetrazol-5-yl-thiomethyl)-3-cephem-4-carboxylic acids, Cefonicid being one of them, by condensation of a tetrazole thiol as is or as sodium salt, with a 7-α-hydroxyacylaminocephalosporanic acid, either salified or in the form of methanolate, in water, in the presence of sodium bicarbonate. The reaction products are collected by aqueous phase acidification and passed through ionic exchange resins.

The corresponding disodium salts are obtained by salification with sodium methoxide in methanol, or by ion exchange chromatography of their aqueous solutions, followed by further purification by precipitation from alcoholic solvents and freeze-drying.

Cefonicid was prepared in particular from D-mandelamidocephalosporanic acid methanolate and from the sodium salt of 1-sulphomethyltetrazole-5-thiol.

The aforementioned U.S. Pat. No. 4,159,373 also discloses the preparation of Cefonicid α-formyloxy derivative, an useful intermediate for the synthesis of same, by acylation of 7-amino-3-(1-sulphomethyltetrazol-5-yl-thiomethyl)-3-cephem-4-carboxylic acid with the formyl ester of D-mandelic acid chloride, in anhydrous dimethylformamide, in the presence of triethylamine.

Cefonicid and its analogues can be obtained from the corresponding formyl derivatives by deformylation in the presence of basic or acid catalysts.

U.S. Pat. No. 4,576,937 generally states that Cefonicid monosodium salt can be prepared by treating its O-formyl derivative with dilute acids, e.g. dilute hydrochloric acid; however, it neither reports illustrative examples nor specifies the actual reaction conditions. The method disclosed in patent application PCT 17600/92 is based on the enzymatic hydrolysis of 7-α-formyloxyacylamino cephalosporins substituted in position 3 with 1-sulphomethyl-tetrazolylthiomethyl groups, including Cefonicid, and of other derivatives with a protected hydroxyl group.

This patent application also exemplifies a synthesis of the aforesaid α-formyl derivatives by acylation of the appropriate 7-aminocephalosporanic nucleus with O-formylmandeloyl chloride, in water, in the presence of sodium bicarbonate.

European patent application No. 0156771 reports an example of deformylation of 7-D-mandelamido-cephalosporins O-formyl derivatives by treatment with acids in the presence of alcohols. Furthermore it discloses the acylation of 7-aminocephalosporanic nuclei with thioesters of D-mandelic acid with a protected hydroxyl group.

Cefonicid preparation is based, in particular, on the use of a thioester of O-formyl-D-mandelic acid and on acylation being carried out in anhydrous dimethylformamide in the presence of triethylamine. Formylated Cefonicid is isolated as a disodium salt, transformed into the corresponding acid by passage through acidic ionic exchange resins, converted into monosodium salt by treatment with sodium 2-ethyl hexanoate, and deformylated in methanol by treatment with concentrated hydrochloric acid or with strongly acidic ionic exchange resins. After addition of NaOH and isopropanol, Cefonicid is precipitated from the reaction mixture as a disodium salt.

The aforesaid methods have several disadvantages, one being that the reaction mixtures produced under the known acylation conditions are intensely coloured. Said inconvenience is particularly evident when operating in dimethylformamide/triethylamine and in water/sodium bicarbonate at 70° C. The undesired colour of acylation intermediates does not fade away in the final cephalosporins. It follows that long, laborious and not always successful purification procedures are required to obtain pharmaceutically acceptable products.

As concerns the methods of deformylation already known, those based on the treatment with alkalis cause degradation of 7-α-formyloxyacylamino cephalosporins and of their deprotected products with consequent decrease in yields; conversely, under neutral or slightly acid conditions, the product stability increases, but the hydrolysis rate decreases considerably.

Furthermore, the presence of high amounts of methanol in the deformylation medium is undoubtedly a hindrance to the recovering of the deformylated product: therefore, the desired product may be properly recovered only if methanol is eliminated from the reaction mixture.

The recovery of the final products is often hard to do, unpractical from the industrial point of view, and economically unprofitable, as it requires purifications by ion exchange chromatography (cf. U.S. Pat. No. 4,159,373) or laborious conversions of disodium salts into acids and then into monosodium salts (cf. EP-A 0156771).

Furthermore, solvent traces can be hardly eliminated even by sophisticated methods, such as e.g. freeze-drying.

SUMMARY

The Assignee has found a new process forming the object of the present invention. Said process, which can be applied to commercial scale plants, obviates the disadvantages of the procedures already known, as it gives high yields of highly pure 7-α-hydroxyacylamino cephalosporins of formula (I)

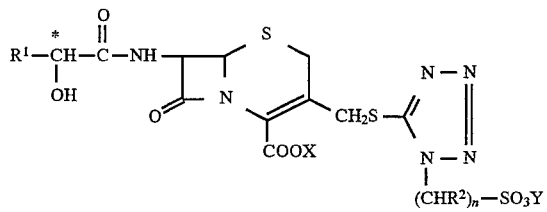

wherein $R^1$ is selected from the group consisting of phenyl group optionally substituted with from 1 to 3 substituents selected from the group consisting of halogens and hydroxyl groups, aromatic or non-aromatic heterocycle having from 4 to 7-atoms in the ring, dihydrophenyl, cyclohexyl, hydroxymethyl, formamido, ureido and carboxymethylamino group;

Examples of phenyl groups are phenyl, hydroxyl-monosubstituted phenyl, 3-fluoro-4-hydroxymethyl.

The aromatic heterocyclic groups may be, in particular, the thionyl group, as well as the pyridinyl, furanyl, pyrrolyl, 1,2,3-triazolyl, 1,2,4-triazolyl, imidazolyl, thiazolyl, thiadiazolyl, pyrimidinyl, oxazolyl, triazinyl, tetrazolyl groups as are or variously substituted.

The non-aromatic heterocyclic groups may be azetidinyl, oxetanyl, thienyl, piperidinyl, piperazinyl, imidazolidinyl, oxazolidinyl, pyrrolidinyl, tetrahydropyrimidinyl, dihydrothiazolyl, and hexahydroazepinyl.

Aromatic and non-aromatic heterocyclic groups may be substituted e.g. with the following groups: C=O, halogens, hydroxy, nitro, amino, cyano, trifluoromethyl, $C_1$–$C_4$ alkyl, $C_1$–$C_4$ alkoxy, phenyl, substituted phenyl.

$R^2$ is hydrogen or a linear or branched alkyl group containing from 1 to 12 carbon atoms;

n is a whole number from 1 to 10;

X and Y, equal or different, are hydrogen or pharmaceutically acceptable cations.

X and Y may be, for example, cations of alkali metals or of alkaline earth metals, such as sodium, potassium, and calcium, or other cations, such as ammonium, or cations of organic amines.

Compounds of formula (I) contain in the side chain at 7-position of the cephem nucleus, an asymmetric carbon atom (marked with an asterisk): therefore, they may be present in the D- or L- form or mixtures thereof.

The process of this invention comprises the following steps:

a) acylating a 7-amino-3-cephem-4-carboxylic acid derivative of formula (II)

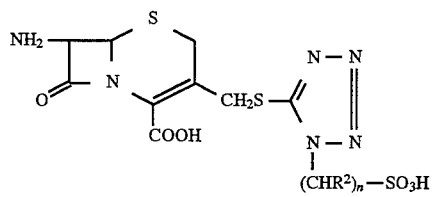

where $R^2$ and n are as defined above, by treating it with a formyl derivative of formula (III)

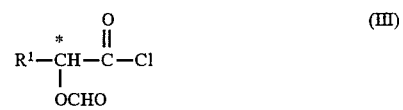

where $R^1$ is as defined above, in a suitable diluent, while maintaining the pH between 6.5 and 7.0 by addition of a proton acceptor;

adding water at the reaction end (should it be not already contained in the diluent) and washing the resulting aqueous phase with an organic solvent;

b) deformylating by treating the aqueous solution obtained in a) with an acid, at pH comprised between 0.5 to 1.5;

c) subjecting the acid aqueous phase obtained in b) to differential extraction, comprising at least one extraction of the aqueous phase with an organic solvent, salting out of the residual acid aqueous phase, followed by extraction with an aprotic solvent selected among tetrahydrofuran, methylethylketone, and acetonitrile;

d) evaporating the aprotic solvent, thus obtaining the derivative of formula (I) wherein X=Y=H, which is subjected to salification in a non-aqueous medium, when the product of formula (I), wherein X and Y, equal or different, are pharmaceutically acceptable cations, is desired.

By methods already known, e.g. treatment with acidic ionic exchange resins, salts of formula (I) (wherein X and Y are cations) obtained from step d) can give the corresponding diacids (X=Y=H), which, by partial salification, can give the mono-salts, as described in EP-A 0156771 with regard to Cefonicid.

Further, it is reported the preparation of the aforesaid derivative of formula (II) by treatment of 7-aminocephalosporanic acid with tetrazole thiol of formula (IV)

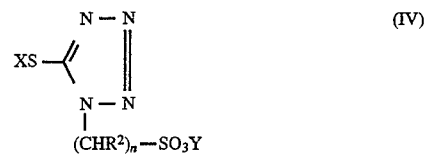

where $R^2$ and n are as defined above, X and Y, identical or different, are pharmaceutically acceptable cations, in an aprotic organic solvent, in the presence of $BF_3$, at a temperature of $-10°$ C. to $+5°$ C., followed by treatment with water, at pH 3.

It is preferred practice to use derivative of formula (IV) wherein X=Y=Na and carry out the reaction in acetonitrile at 0° C.

DETAILED DESCRIPTION OF THE INVENTION

Several 7-amino-3-cephem-4-carboxylic derivatives of formula (II) and formyl derivatives of formula (III) are intermediates already known: they are commercially available or, in any case, can be prepared by methods disclosed in patents and scientific papers.

The absolute configuration of the asymmetric carbon atom in products of formula (I) corresponds to the configuration of the acylating agent of formula (II) used for their synthesis.

In the acylating step, the diluent may be selected, in particular, between tetrahydrofuran/water mixtures and dimethylacetamide.

Protons acceptor is an organic or inorganic base, preferably selected from the group consisting of $NH_3$, NaOH, $NaHCO_3$, $Na_2CO_3$, triethylamine, and mixtures thereof.

In the present invention, it is preferred practice to use a tetrahydrofuran/water mixture (40/60 to 60/40 v/v); typically, ammonia is the protons acceptor.

It is also preferred practice according to the present invention to use dimethylacetamide in the presence of bistrimethylsilylacetamide (BSA); typically, triethylamine is the protons acceptor.

The amount of BSA used is adequate for solubilizing the acid of formula (II) through formation of the corresponding silyl derivative.

Acylation is carried out at temperatures ranging from −10° C. to +50° C., preferably from 0° C. to +5° C.

The present acylation conditions are particularly mild. Under said conditions the acid of formula (II) is adequately solubilized and the formation of coloured products is reduced drastically and in any case to acceptable levels. As already mentioned, intense colouring is one of the disadvantages of the acylation methods already known. The solution resulting from acylation contains acylation product of Formula (V) in salified form

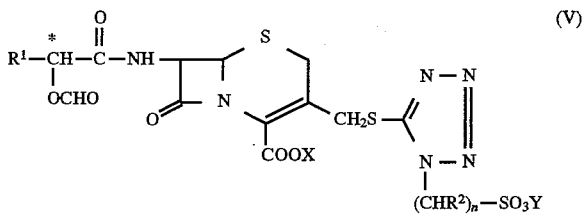

where $R^1$, $R^2$ and n are as defined above and X and Y, identical or different, are cations corresponding to the protons acceptors used in a).

The solution leaving acylation is subjected to deformylation by simple acid addition: the reaction solvent has not to be changed and isolation and purification of the intermediate are not required.

The acid may be an inorganic acid, e.g. hydrochloric acid or sulphuric acid, or an organic acid, e.g. trifluoroacetic acid or trifluoromethane sulphonic acid.

The deformylation conditions are critical: the ranges of temperature and of pH adopted allow an optimization of the reaction rate (too low at pH values above 1.5 and at temperatures below 0° C.) and minimize the formation of undesired by-products.

Furthermore, since no alcohols are used, the problem represented by their elimination from the reaction mixtures is avoided.

Deformylation is preferably carried out in the presence of hydrochloric acid. The temperature can vary from 0° C. to +60° C., the reaction times being comprised between 2 to 48 hrs. Under more preferred conditions, deformylation is carried out at pH comprised between 0.8 and 1.2 (more preferably 1) at a temperature of +25° C.–35° C. (more preferably +30° C.) thus requiring reaction times of from 12 to 20 hrs.

It is worth noting that the deformylation conditions selected according to the present invention allow to minimize the formation of a by-product more polar than the desired product.

Particularly, the present deformylation conditions allow to obtain cephalosporins in such a chemically pure form that no crystallization or chromatographic purification is needed to obtain a product having the required standard quality.

In the case of Cefonicid, the polar by-product is the one having a retention time (Rt) value of 1.7 under the MPLC analytical conditions reported in USP XXII and Supplements for the analysis of Cefonicid.

The maximum acceptable amount of this polar by-product for Cefonicid is of about 1.5–2%.

The present process allows to obtain cephalosporins with a maximum content of this polar by-product even lower than 1%.

Therefore, in the case of Cefonicid, the final cephalosporin is not only acceptable according to the standards fixed by pharmacopoeias, but even of better quality than the products sold on the market, which contain said by-product in amounts of 1–1.6%.

In particular, when the deformylation is carried out at pH comprised between 0.8–1.2 and temperatures between +25°–+35° C., the amount of this by-product in the reaction mixture coming from deformylation is of about 4–6%, it decreases to values about 1.5–2% in the reaction mixture obtained from the extraction step c), and it further decreases in the salification according to step d).

Operating out of the range of deformylation conditions selected by the Assignee, higher amounts of this polar by-product would be obtained, thus affording a worst quality product and/or making necessary additional purification stages to decrease its content within acceptable values.

The Assignee has particularly found that the formation of the above mentioned polar by-product is increased lowering pH, as well as raising temperature and lengthening the reaction times.

According to a further preferred embodiment of the present invention, the reaction mixture coming from the acylation step a), before the deformylation step b), is subjected to treatment under vacuum to eliminate most of the organic solvents therein contained, preferably up to a maximum content of 2% weight by volume.

The organic solvents present in the reaction mixture coming from acylation comprise either the organic solvents used as diluents in the acylation and the residues of those used in step a) to wash the aqueous phase at the end of the reaction. Their amount in the reaction mixture coming from acylation is typically of about 6–7% (weight by volume).

The treatment under vacuum can be suitably effected by maintaining the reaction mixture under stirring at a reduced pressure comprised between 3999 and 10664 Pa (corresponding to 30 to 80 mmHg), at temperatures comprised between +20° and +40° C., for times comprised between 10 and 60 minutes.

Unexpectedly, when the above mentioned treatment under vacuum is effected, the reaction times in the deformylation step are considerably reduced, and, what is even more surprising, the content of the above mentioned polar by-product is further lowered.

As a matter of fact, when deformylation is carried out at pH 0.9–1.1, at +30° C.–+35° C., the reaction is completed within about 12–16 hours, and under these conditions the polar by-product formation is contained within 2.5–4% (amount in the crude reaction mixture).

When the treatment under vacuum is effected, 6–8 hours are sufficient to obtain complete deformylation under the same pH and temperature conditions, and the amount of by-product in the crude reaction mixture thus obtained is of about 2–2.5%.

This is a significant improvement, since in the subsequent extraction phase according to step c) the polar by-product drops to 1–2%, and after the salification step even below 1%.

Differential extraction is particularly important: in this stage, products of formula (I) wherein X=Y=H, are extracted in extremely pure form being separated from the degradation products formed during deformylation, which remain in the aqueous phase.

The organic solvents used in the extraction stages (at the end of acylation as well as of deformylation) are water-immiscible solvents, e.g. halogenated solvents such as chloroform and methylene chloride.

The solvent preferably used in the extraction after salting out is tetrahydrofuran.

Salting out is a well known technique in laboratory practice consisting in the addition of an inorganic salt, usually NaCl, to an aqueous solution, in an amount adequate for exceeding its solubility product and, therefore, affording to deposit formation.

Salting out allows a practically complete extraction of products of formula (I) which otherwise, due to their very high solubility in water, would be extracted incompletely.

Salification may be carried out through known methods.

Wishing to obtain sodium salts, a preferred method consists in concentrating the organic solution obtained from step c) so to remove most of the aprotic solvent and treating the resulting product, generally an oil, with sodium 2-ethylhexanoate in a solvent selected from the group consisting of tetrahydrofuran, methanol, ethanol, acetone, methyl ethyl ketone and mixtures thereof.

Particularly preferred is the use of an acetone/ethanol mixture in ratios comprised from 30:70 to 70:30, preferably 2:1 volume by volume.

The present process is suitable for the preparation of the derivatives of formula I wherein $R^2$ is hydrogen, n is 1, X=Y=Na and $R^1$ is phenyl, esahydrophenyl or 4-chlorophenyl.

The present process is particularly suitable for the production of Cefonicid, in particular as disodium salt [product of formula (I) wherein $R^1$ is phenyl, the asterisked carbon atom has D-configuration, $R^2$ is hydrogen, n is 1, and X=Y=Na].

Another advantage of the present process is that it can be very profitably applied to commercial scale plants, since toxic solvents, such as e.g. methanol, are not used and purifications through ionic exchange resins and laborious monosodium salts-disodium salts interconversions are not required.

Products of formula (I) obtained by the process under this invention are chemically very pure. The water and solvents content can be easily eliminated by conventional techniques, e.g. freeze-drying.

The following examples are illustrative only; in no event are they to be regarded as limiting the scope of the invention.

In all the reported examples, pH has been measured with an Ingold 405/60TS7 −120/9.48 electrode.

EXAMPLE 1

Preparation of 7-amino-3-[sulphomethyl-1-H-tetrazol-5-yl-thiomethyl]-3-cephem-4-carboxylic acid 1-Sulphomethyl-5-mercapto-1,2,3,4-tetrazole disodium salt (9.5 g) suspended in acetonitrile (33.5 ml) was added with 7-amino-cephalosporanic acid (10 g) and the resulting mixture was cooled to 0° C. The suspension obtained was added with a 15% $BF_3/CH_3CN$ solution and the reaction mixture was maintained at 0° C. for 8 hrs. The solution was added with water (10 ml) yielding a precipitate which was filtered and washed with acetonitrile.

The product, dissolved in water (55 ml), was treated with carbon TAIKO® SBW 10/15 and, after 30 min of contact, was filtered. The product was precipitated with ammonia (1:1) and pH adjusted to 3.0. Two hours later, the product was filtered, washed with water, then with aceton and dried.

13.0 g of 7-amino-3-[sulphomethyl-1-H-tetrazol-5-yl-thiomethyl]-cephalosporanic acid was obtained.

Yield 92%; HPLC purity 99%.

$^1$-NMR ($D_2O$): δ(ppm): 3.64 (ABq, J=18 Hz, 2H); 4.26 (ABq, J=14 Hz, 2H); 5.03 (d, J=4.6 Hz, 1H); 5.15 (d, J=4.6 Hz, 1H); 5.48 (s, $NCH_2SO_3^-$, 2H).

EXAMPLE 2

Preparation of 7-(D-2-hydroxy-2-phenylacetamido-3-[1-sulphomethyl-1-H-tetrazol-5-yl-thiomethyl]-3-cephem-4-carboxylic acid disodium salt [derivative of formula (I) wherein $R^1$ is phenyl, $R^2$ is H, n=1, X=Y=Na, wherein the carbon atom marked with an asterisk has D configuration]

a) Acylation: 7-amino-3-[sulphomethyl-1-H-tetrazol-5-yl)thiomethyl]3-cephem-4-carboxylic acid (10 g) was suspended in a mixture of deionized water (80 ml) and tetrahydrofuran (60 ml). The resulting mixture was cooled to 2° C. and dissolved by addition of dilute ammonia (1:1) (3.5 ml).

The perfectly clear solution was added, at a temperature of 0° C.±1° C., with D (−) formylmandeloyl chloride (5.3 g) dissolved in tetrahydrofuran (THF) (20 ml), while maintaining the pH at 6.5–7.0 by gradual addition of 1:1 dilute ammonia.

The reaction was allowed to proceed at 0° C. for 30′, then the solution was washed with 2×15 ml methylene chloride.

b) Deformylation: the solution was acidified with conc. HCl (3.5–4.0 ml) at pH 1.0, maintained at +30° C. hrs 20 hrs, then cooled to 20° C., and decolourized on carbon TAIKO® SBW 10/15 (1 g) under stirring for 30′ (The reaction is completed after 12–16 hours).

c) Differential extraction: the acid solution was filtered and washed again with 2×30 ml methylene chloride, then added with sodium chloride (40 g), and allowed to stir until dissolution of most added salt. The resulting mixture was extracted with THF ml) and again with 2×23 ml THF.

d) Solvent evaporation and salification: the organic extracts were collected together and concentrated to small volume (oil). The oil was taken up with EtOH (20 ml), concentrated again, taken up with acetone (50 ml) and absolute EtOH (25 ml), and decolourized on TAIKO® SBW 10/15 (1 g).

The product in solution was precipitated as disodium salt by addition of a sodium 2-ethylhexanoate solution (8.2 g dissolved in 23.5 ml acetone) under vigorous stirring.

One hour later the precipitate was collected, washed with an acetone/EtOH mixture and then with acetone, and dried under vacuum (e.g. by water pump) at 40° C. to constant weight.

11.8 g of product having the following chemico-physical properties were obtained:

chemical purity=97%, determined by HPLC according to the method described in USP XXII and Supplements thereof;

K.F.=4.5% (K.F.=water content according to Karl Fisher method); solvent residues=3.5%

The sample was freeze-dried and 10.6 g of product with chemical purity (HPLC) of 97.0% and K.F. of 1.5% was obtained.

Elemental analysis as:

| Elemental analysis as: | | |
|---|---|---|
|  | % calculated | % found |
| $C_{18}$ | 36.86 | 36.97 |
| $H_{16}$ | 2.75 | 2.89 |
| $N_6$ | 14.33 | 13.97 |
| $S_3$ | 16.40 | 16.24 |
| $Na_2$ | 7.84 | 7.66 |

$[\alpha]^D = -40°$ [c=1%; perfectly clear MeOH]

$^1$H-NMR ($D_2O$): δ(ppm): 3–33 and 3.65 (dd, J=17–7 Hz, 2H); 4.40 and 4.08 (dd, J=13.4 Hz, 2H); 5.02 (d, J=4.67 Hz, 1H); 5.26 (s, 1H); 5.47 (dd, 2H); 5.58 (d, J=4.67 Hz, 1H); 7.45 (m, 5H).

EXAMPLE 3

Preparation of 7-[2-(R,S)]-2-hydroxy-2-phenylacetamido-3-[1-sulphomethyl-1-H-tetrazol-5-yl)-thiomethyl]-3-cephem-4-carboxylic acid disodium salt [racemic form of the derivative of formula (I) wherein $R^1$ is phenyl, $R^2$ is H, n=1, X=Y=Na]

a) Acylation: 7-amino-3-[sulphomethyl-1-H-tetrazol-5-yl)thiomethyl]3-cephem-4-carboxylic acid (16.38 g) was suspended in a mixture of deionized water (131 ml) and tetrahydrofuran (98 ml). The resulting mixture was cooled to 0° C. and dissolved by addition of dilute ammonia (1:1) (18.4 ml). [1:1 dilute ammonia is obtained by diluting 1:1 commercially available aqueous solutions with an ammonium hydroxide content of 25% weight by volume, obtaining an aqueous solution with a content of ammonium hydroxide of about 14% weight by volume].

(R.S)-O-formylmandeloyl chloride (13.8 g) dissolved in tetrahydrofuran (THF) (33 ml) is added, while maintaining the pH at 6.5–7.0 by gradual addition of 1:1 dilute ammonia.

The reaction was allowed to proceed at 0° C., then the solution was washed with methylene chloride, analogously to what described For Example 2.

Deformylation, differential extraction, solvent evaporation and salification were effected analogously to what described in Example 2.

19 g of product having the following chemico-physical properties were obtained:

| Elemental analysis as: | | |
|---|---|---|
|  | % calculated | % found |
| $C_{18}$ | 36.86 | 36.49 |
| $H_{16}$ | 2.75 | 3.02 |
| $N_6$ | 14.33 | 14.12 |
| $S_3$ | 16.40 | 15.99 |
| $Na_2$ | 7.84 | 7.98 |

$^1$H-NMR ($D_2O$): δ(ppm): 3.39 (m, 1H) and 3.68 (m, 1H): cyclic $CH_2S$; 4.15 (dd, 1H) and 4.40 (dd, 1H): exocyclic $CH_2S$; 5.05 (m, 1 H, CH at position 6); 5.26 (s, 1H) and 5.28 (s, 1H): CHOH (R.S); 5–50 (m, 2H, $CH_2SO_3$); 5.60 (m, 1H, CH at position 7); 7.47 (m, 5H, aromatic protons).

EXAMPLE 4

Preparation of 7-[2-(R)-2-hydroxy-2-esahydrophenylacetamido-3-[1-sulphomethyl-1-H-tetrazol-5yl)-thiomethyl]-3-cephem-4-carboxylic acid disodium salt [derivative of formula (I) wherein $R^1$ is cycloexyl, $R^2$ is H, n=1, X=Y=Na, wherein the carbon atom marked with an asterisk has R configuration]

a) Acylation: 7-amino-3-[sulphomethyl-1-H-tetrazol-5-yl)thiomethyl]3-cephem-4-carboxylic acid (6.33 g) was suspended in a mixture of deionized water (51.3 ml) and tetrahydrofuran (38.5 ml). The resulting mixture was cooled to 0° C. and dissolved by addition of 14% dilute ammonia (4.7 ml).

2-(R)-O-formyl-2-esahydrophenyl acetic acid chloride (5.29 g) (0.026 moles) dissolved in tetrahydrofuran (THF) (37.7 ml) is added, while maintaining the pH at 6.5–7.0 by gradual addition of 1:1 dilute ammonia.

The reaction was allowed to proceed at 0° C., then the solution was washed with methylene chloride, analogously to what described for Example 2.

Deformylation, differential extraction, solvent evaporation and salification are effected analogously to what described in Example 2.

6.8 g of product having the following analytical characteristics were obtained:

| Elemental analysis as: | | |
|---|---|---|
|  | % calculated | % found |
| $C_{18}$ | 36.48 | 35.38 |
| $H_{22}$ | 3.75 | 3.88 |
| $N_6$ | 14.18 | 13.72 |
| $S_3$ | 16.23 | 15.98 |
| $Na_2$ | 7.76 | 7.68 |

$^1$H-NMR ($D_2O$): δ(ppm): 1.21 (m, 5H); 1.70 (m, 6H); 3.47 (d, 1H, J=17.7 Hz) and 3.78 (d, 1H, J=17.7 Hz): cyclic $CH_2S$; 4.06 (d, 1H): CHOH; 4.15 (d, 1H, J=13.5 Hz) and 4.45 (d, 1H, J=13.5 Hz): exocyclic $CH_2S$; 5.11 (s, 1 H, CH at position 6); 5.55 (s, 2H, $CH_2SO_3$); 5.64 (d, 1H, CH at position 7).

EXAMPLE 5

Preparation of 7-[2-(D.L)-2-hydroxy-2-(4-chlorophenyl)acetamido-3-[1-sulphomethyl-1-H-tetrazol-5-yl)-thiomethyl]-3-cephem-4-carboxylic acid disodium salt [racemic form of the derivative of formula (I) wherein $R^1$ is 4-chlorophenyl, $R^2$ is H, n=1, X=Y=Na]

a) Acylation: 7-amino-3-[sulphomethyl-1-H-tetrazol-5-yl)thiomethyl]3-cephem-4-carboxylic acid (6.33 g) was suspended in a mixture of deionized water (51.3 ml) and tetrahydrofuran (38.5 ml). The resulting mixture was cooled to 0° C. and dissolved by addition of 1:1 dilute ammonia (4.7 ml).

2-(R,S)-O-formyl-(4-chlorophenyl) acetic acid chloride (5.4 g) dissolved in tetrahydrofuran (THF) (37.7 ml) is added, while maintaining the pH at 6.5–7.0 by gradual addition of 1:1 dilute ammonia.

The reaction was allowed to proceed at 0° C., then the solution was washed with methylene chloride, analogously to what described for Example 2.

Deformylation, differential extraction, solvent evaporation and salification are effected analogously to what described in Example 2.

6.4 g of product having the following analytical characteristics were obtained:

| Elemental analysis as: | | |
|---|---|---|
| | % calculated | % found |
| $C_{18}$ | 34.82 | 33.76 |
| $H_{15}$ | 2.43 | 2.69 |
| Cl | 5.71 | 5.57 |
| $N_6$ | 13.53 | 13.30 |
| $S_3$ | 15.49 | 15.20 |
| $Na_2$ | 7.40 | 7.61 |

$^1$H-NMR ($D_2O$): δ(ppm): 3.40 (m, 1H) and 3.70 (m, 1H): cyclic $CH_2S$; 4.10 (dd, 1H) and 4.40 dd, 1H): exocyclic $CH_2S$; 5.02 (m, 1 H, CH at position 6); 5.25 (s, 1H) and 5.27 (s, 1H); (D,L) CHOH; 5.48 (m, 2H, $CH_2SO_3$); 5.58 (m, 1H, CH at position 7); 7.45 (m, 4H, aromatic protons).

EXAMPLE 6

Preparation of 7-(D)-2-hydroxy-2-phenylacetamido-3-[1-sulphomethyl-1-H-tetrazol-5-yl)-thiomethyl]-3-cephem-4-carboxylic acid disodium salt [derivative of formula (I) wherein $R^1$ is phenyl, $R^2$ is H n=1, X=Y=Na, wherein the carbon atom marked with an asterisk has D configuration a) Acylation: 7-amino-3-[sulphomethyl-1-H-tetrazol-5-yl)thiomethyl]3-cephem-4-carboxylic acid (10 g) was subjected to acylation as described in Example 1.

The crude reaction mixture, after washing with methylene chloride, is left under vacuum (6695 Pa=50 mmHg), at 30° C. for 30 minutes, while stirring.

Most of the organic solvent left in the aqueous phase (about 60–70 g each liter of aqueous reaction mixture) is thus removed.

The aqueous solution thus obtained is then subjected to deformylation.

b) Deformylation: the aqueous solution is acidified with concentrated HCl (3.5–4.0 ml) at pH 0.9–1.1 and maintained at +30°±1° C. for 6–7 hours.

HPLC analysis, performed after 6 hours with the method described for cefonicid in USP XXII and Supplements, gave the following results:

deformylated product (Area %) 96.1%; Rt (retention time)=about 3.2 minutes;

formylated product (Area %) 1.7%; Rt=8 minutes;

polar by-product (Area %) 1.9%; Rt=about 1.7 minutes;

unidentified by-product (Area %) 0.5%; Rt=about 3.85 minutes.

After cooling to +20° C., the reaction mixture is treated under stirring for 30 minutes with carbon TAIKO® SBW 10/15 (1 g). Steps c) and d) were effected analogously to what described in Example 2.

12.1 g of product having the following analytical characteristics were obtained:

HPLC purity=98.7%.

Total impurities=1.3%

HPLC titre=96.5% (calculated on the dried basis, and corresponding to 89.3% of the relative acid form)

$[\alpha]_D^{20}$=−41.9 (C=1%; MeOH)

Water (K.F.)=4.71%

Na=7.93% (on the dried product) (theoretical=7.84%)

Solvents: EtOH=0.68%

Aceton=3.13%.

We claim:

1. A process for the preparation of 7-α-hydroxyacylamino cephalosporins of formula (I)

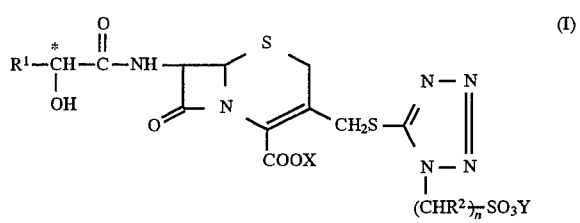

wherein $R^1$ is selected from the group consisting of (a) phenyl which may be optionally substituted with from 1 to 3 substituents selected from the group consisting of halogen and hydroxyl groups; and (b) cyclohexyl;

$R^2$ is hydrogen or a linear or branched alkyl group containing from 1 to 12 carbon atoms:

n is a whole number from 1 to 10;

X and Y, are equal or different, and are elected from the group hydrogen or pharmaceutically acceptable cations, said process comprising the following steps:

a) acylating a 7-amino-3-cephem-4-carboxylic acid derivative of formula (II):

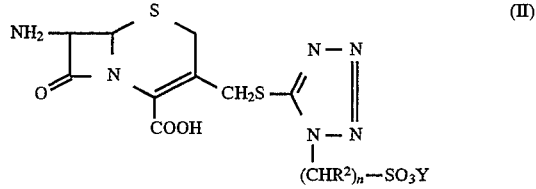

where $R^2$ and n are as defined above, by treating said derivative of formula (II) with a formyl derivative of formula (III):

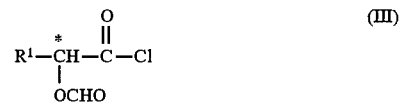

where $R^1$ is as defined above, in a tetrahydrofuran/water mixture, while maintaining the pH between 6.5 and 7.0 by the addition of a proton acceptor; and at the end of acylation washing the resulting aqueous phase with a halogenated solvent;

b) deformylating the aqueous solution obtained in step a) with an acid, at a pH between 0.5 to 1.5 and at a temperature between 0° and 60° C.;

c) subjecting the acidic aqueous phase obtained in step b) to at least one extraction of the aqueous phase with a halogenated organic solvent, followed by salting out of the residual acidic aqueous phase, followed by extraction with an aprotic solvent selected from the group consisting of tetrahydrofuran, methylethylketone, and acetonitrile;

d) evaporating the aprotic solvent, to obtain the derivative of formula (I) wherein X=Y=H.

2. The process as claimed in claim 1, wherein phenyl is selected from the group consisting of phenyl, hydroxylmonosubstituted phenyl and 3-fluoro-4-hydroxymethyl.

3. The process according to claim 1, wherein in step a) the protons acceptor is an organic or inorganic base selected from the group consisting of $NH_3$, NaOH, $NaHCO_3$, $Na_2CO_3$, triethylamine and mixtures thereof.

4. The process according to claim 1, wherein step a) is carried out at temperatures from 0° C. to +5° C.

5. The process according to claim 1, wherein step a) is carried out between 0° and 5° C.

6. The process according to claim 5, wherein step a) is carried out with a tetrahydrofuran/water mixture (40/60 to 60/40 v/v) as a diluent and ammonia as protons acceptor.

7. The process according to claim 1, wherein deformylation is carried out with an acid selected from the group consisting of hydrochloric acid, sulphuric acid, trifluoroacetic acid and trifluoromethane sulphonic acid.

8. The process as claimed in claim 7, wherein the acid is hydrochloric acid.

9. The process according to claim 1, wherein deformylation is carried out at pH comprised between 0.8 to 1.2, and at temperatures comprised between +25° and +35° C.

10. The process according to claim 9, wherein pH is 1 and the temperature is +30 C.

11. The process according to claim 1, wherein the reaction mixture coming from the acylation step a), before the deformylation step b), is subjected to treatment under vacuum so to decrease the maximum content of the organic solvents therein contained down to 2% weight by volume.

12. The process according to claim 11, wherein the treatment under vacuum is effected by maintaining the reaction mixture under stirring at a reduced pressure comprised between 3999 to 10664 Pa (corresponding to 30 to 80 mmHg), at temperatures comprised between +20° and +40° C., for times comprised between 10 and 60 minutes.

13. The process according to claim 1, wherein the halogenated solvent used in a) and c) is selected between chloroform and methylene chloride.

14. The process according to claim 1, wherein the solvent used for the extraction following the salting out is tetrahydrofuran.

15. The process according to claim 1, wherein the organic solution obtained in c) is concentrated and the salification is carried out by treating the product obtained with sodium 2-ethylhexanoate, in a solvent selected from the group consisting of tetrahydrofuran, methanol, ethanol, acetone, methylethylketone and mixtures thereof.

16. The process according to claim 15, wherein the solvent is an acetone/ethanol mixture in ratios comprised between 30:70 to 70:30.

17. The process of claim 1 wherein the product obtained in step d) is salified in a non-aqueous medium to form a salt wherein X and Y are the same or different cations.

18. The process as claimed in claim 1, wherein $R^1$ is esahydrophenyl or 4-chlorophenyl, $R^2$ is hydrogen, n is 0, and X=Y=Na.

19. A process for the preparation of 7-α-hydroxyacylamino cephalosporins of formula (I)

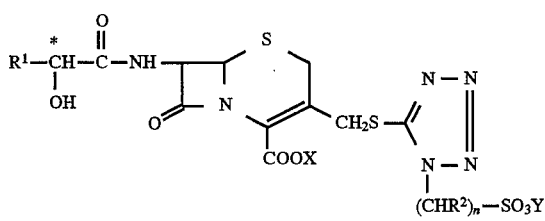

wherein $R^1$ is phenyl, $R^2$ is hydrogen and n is 1;
X and Y may be the same or different, and are hydrogen or pharmaceutically acceptable cations,
said process comprising the following steps:
a) acylating a 7-amino-3-cephem-4-carboxylic acid derivative of formula (II):

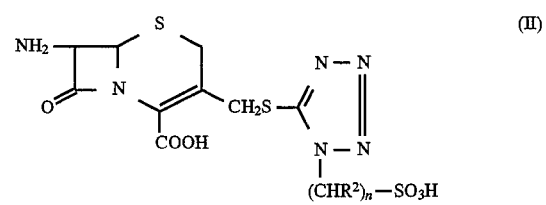

where $R^2$ and n are as defined above, by treating said derivative of formula (II) with a formyl derivative of formula (III)

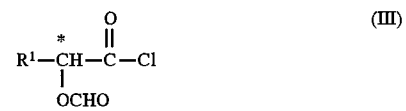

where $R^1$ is as defined above, in a tetrahydrofuran/water mixture while maintaining the pH between 6.5 and 7.0 by the addition of a proton acceptor; and at the end of acylation washing the resulting aqueous phase with a halogenated solvent;

b) deformylating the aqueous solution obtained in step a) with an acid, at a pH between 0.5 to 1.5 and at a temperature between 0° and 60° C.;

c) subjecting the acidic aqueous phase obtained in step b) to at least one extraction of the aqueous phase with a halogenated organic solvent, followed by salting out of the residual acidic aqueous phase, followed by extraction with an aprotic solvent selected from the group consisting of tetrahydrofuran, methylethylketone, and acetonitrile;

d) evaporating the aprotic solvent, to obtain the derivative of formula (I) wherein X=Y=H.

20. The process as claimed in claim 19, wherein the carbon atom marked with an asterisk has a D-configuration, and X=Y=Na.

21. The process according to claim 19 wherein in step a) the proton acceptor is an organic or inorganic base selected from the group consisting of $NH_3$, NaOH, $NaHCO_3$, triethylamine and mixtures thereof.

22. The process according to claim 20 wherein in step a) the proton acceptor is an organic or inorganic base selected from the group consisting of $NH_3$, NaOH, $NaHCO_3$, triethylamine and mixtures thereof.

23. The process according to claim 19 wherein step a) is carried out at temperatures from 0° C. to +5° C.

24. The process according to claim 20 wherein step a) is carried out at temperatures from 0° C. to +5° C.

25. The process according to claim 19 wherein the acid of formula (I) is solubilized in the acylation medium.

26. The process according to claim 20 wherein the acid of formula (I) is solubilized in the acylation medium.

27. The process according to claim 19 wherein step a) is carried out with a 40:60 to 60:40 by volume mixture of tetrahydrofuran and water.

28. The process according to claim 20 wherein step a) is carried out with a 40:60 to 60:40 by volume mixture of tetrahydrofuran and water.

29. The process according to claim 27 where ammonia is used as a proton acceptor.

30. The process according to claim 19 wherein deformylation is carried out with an acid selected from the group consisting of hydrochloric acid, sulfuric acid, trifluoro acetic acid and trifluoromethane sulfonic acid.

31. The process according to claim 20 wherein deformylation is carried out with an acid selected from the group consisting of hydrochloric acid, sulfuric acid, trifluoric acetic acid and trifluoromethane sulfonic acid.

32. The process as claimed in claim 30 wherein the acid is hydrochloric acid.

33. The process according to claim 19 where deformylation is carried out at a pH between 0.8 and 1.2 and at a temperature between +25° and +35° C.

34. The process according to claim 20 where deformylation is carried out at a pH between 0.8 and 1.2 and at a temperature between +25° and +35° C.

35. The process according to claim 33 wherein the pH is 1 and the temperature is +30° C.

36. The process according to claim 19 wherein the reaction mixture coming from acylation step a), before the deformylation step b), is subjected to treatment under vacuum so as to decrease the maximum content of the organic solvents therein to 2% w/v.

37. The process according to claim 20 wherein the reaction mixture coming from acylation step a), before the deformylation step b), is subjected to treatment under vacuum so as to decrease the maximum content of the organic solvents therein to 2% w/v.

38. The process according to claim 19 wherein the treatment under vacuum is effected by maintaining the reaction mixture under stirring at a reduced pressure comprised between 399 and 10664 Pa at a temperature between +20° and +40° C.

39. The process according to claim 20 wherein the treatment under vacuum is effected by maintaining the reaction mixture under stirring at a reduced pressure comprised between 399 and 10664 Pa at a temperature between +20° and +40° C.

40. The process according to claim 19 wherein the halogenated solvent used in a) and c) is selected from the group consisting of chloroform and methylene chloride.

41. The process according to claim 20 wherein the halogenated solvent used in a) and c) is selected from the group consisting of chloroform and methylene chloride.

42. The process according to claim 19 wherein the solvent used for the extraction following the salting out is tetrahydrofuran.

43. The process according to claim 20 wherein the solvent used for the extraction following the salting out is tetrahydrofuran.

44. The process according to claim 20 wherein the organic solution obtained in c) is concentrated and the salification is carried out by treating the product obtained with sodium 2-ethylhexanoate in a solvent selected from the group consisting of tetrahydrofuran, methanol, ethanol, acetone, methylethyl ketone and mixtures thereof.

45. The process according to claim 44 wherein the solvent is an acetone/ethanol mixture in a ratio between 30:70 to 70:30.

46. The process of claim 19, wherein the product obtained in step d) is salified in a non-aqueous medium to form a salt wherein X and Y are the same or different cations.

47. The process as claimed in claim 19, wherein the working temperature of step (a) is −10°/+50° C.

48. A process for the preparation of 7-α-hydroxyacylamino cephalosporin of formula (I)

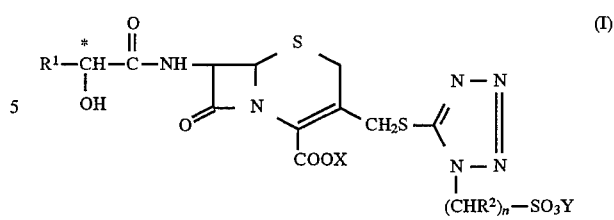

wherein $R^1$ is selected from the group consisting of:
phenyl which may be optionally substituted with 1 to 3 substituents selected from the group consisting of halogens and hydroxyl groups, (b) aromatic or non-aromatic heterocyclic groups selected from the groups consisting of pyridinyl, furanyl, pyrrolyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thienyl, piperidinyl, piperazinyl, imidazolidinyl, oxazolidinyl pyrrolidinyl, tetrahydropyrimidinyl, dihydrothiazolyl and hexhydroazepinyl, wherein said heterocyclic groups may be optionally substituted with groups selected form the group consisting of C=O, halogens, hydroxy, nitro, amino, cyano, trifluoromethyl, $C_1$–$C_4$ alkyl, $C_1$–$C_4$ alkoxy and phenyl;

(c) dihydrophenyl, (d) cyclohexyl, (e) hydroxymethyl, (f) formamido, (g) ureido and (h) carboxymethylamino groups;

$R^2$ is hydrogen or a linear or branched alkyl group containing from 1 to 12 carbon atoms;

n is a whole number from 1 to 10;

X and Y, are equal or different, and are hydrogen or pharmaceutically acceptable cations, comprising the following steps:
a) acylating a 7-amino-3-cephem-4-carboxylic acid derivative of formula (II)

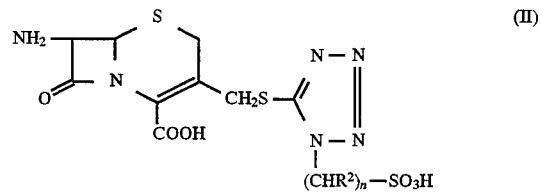

where $R^2$ and n are as defined above, by treating it with a formyl derivative of formula (III)

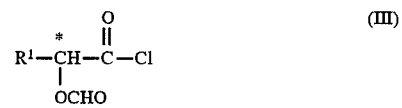

where $R^1$ is as defined above, in a tetrahydrofuran/water mixture, while maintaining the pH between 6.5 and 7.0 by the addition of a proton acceptor; and at the end of acylation washing the resulting aqueous phase with a halogenated solvent;

b) deformylating the aqueous solution obtained in step a) with an acid, at a pH between 0.5 to 1.5, at a temperature between 0° and 60° C.;

c) subjecting the acidic aqueous phase obtained in step b) to at least one extraction of the aqueous phase with a halogenated organic solvent, followed by salting out of the residual acid aqueous phase, followed by extraction with an aprotic solvent selected from the group consisting of tetrahydrofuran, methylethylketone and acetonitrile;

d) evaporating the aprotic solvent, to obtain the derivative of formula (I) wherein X=Y=H, which may be optionally subjected to salification in non aqueous medium, to obtain the product of formula (I), wherein X and Y, are equal or different, and are pharmaceutically acceptable cations.

49. The process as claimed in claim 48, wherein step a) is carried out at a temperature between −10° C. and +50° C.; step b) is carried out at a pH between 0.8 to 1.2, at a temperature between +25° C. and +35° C.

50. The process as claimed in claim 48, wherein step a) is carried out at a temperature between 0° C. and +5° C.

51. The process as claimed in claim 48, wherein in step b) pH is 1 and the temperature is +30° C.

52. The process as claimed in claim 48, wherein the proton acceptor is selected from the group consisting of $NH_3$, NaOH, $NaHCO_3$, triethylamine and mixtures thereof; deformylation is carried out with an acid selected from the group consisting of hydrochloric acid, sulfuric acid, trifluoroacetic acid and trifluoromethanesulfonic acid; salification is effected with sodium 2-ethylhexanoate, in a solvent selected from the group consisting of tetrahydrofuran methanol, acetone, methylethylketone and mixtures thereof.

53. The process as claimed in claim 48, wherein step a) is carried out with a 40:60 to 60:40 by volume mixture of tetrahydrofuran and water; in step b), the acid is hydrochloric acid; the halogenated solvent used in step a) and b) is selected between chloroform and methylene chloride; the solvent used for the extraction following salting out is tetrahydrofuran; the solvent used in salification step is an acetone/ethanol mixture in a ratio between 30:70 and 70:30.

54. The process as claimed in claim 48, wherein the reaction mixture coming from acylation step a), before deformylation step b) is subjected to treatment under vacuum so as to decrease the maximum content of the organic solvents therein to 2% w/v.

55. The process as claimed in claim 54, wherein the treatment under vacuum is effected by maintaining the reaction mixture under stirring at a reduced pressure comprised between 399 and 10664 Pa at a temperature between +20° C. and +40° C.

* * * * *